United States Patent [19]

Miller

[11] 4,427,004

[45] Jan. 24, 1984

[54] ANNULAR FLOW ENTRAINMENT NEBULIZER

[75] Inventor: Kenneth G. Miller, Palatine, Ill.

[73] Assignee: Viridan Inc., Wheeling, Ill.

[21] Appl. No.: 244,012

[22] Filed: Mar. 16, 1981

[51] Int. Cl.[3] .............................................. A61M 11/00

[52] U.S. Cl. .......................... 128/200.21; 128/203.25; 128/203.27; 261/DIG. 65; 219/275; 239/338

[58] Field of Search ...................... 128/200.11, 200.14, 128/200.18, 200.21, 203.12, 203.26, 203.27, 204.14; 261/142, 78 A, DIG. 65; 219/272, 273, 275; 239/135, 338

[56] References Cited

U.S. PATENT DOCUMENTS

| | | | |
|---|---|---|---|
| 2,084,299 | 6/1937 | Borden | 128/203.27 |
| 3,675,360 | 7/1972 | Pierce | 219/275 |
| 3,724,454 | 4/1973 | Brown | 128/200.21 |
| 3,744,722 | 7/1973 | Burns | 128/200.18 |
| 3,820,540 | 6/1974 | Hirtz et al. | 128/203.27 |
| 3,944,635 | 3/1976 | Siegenthaler | 261/DIG. 65 |
| 4,299,355 | 11/1981 | Hakkinen | 128/200.21 |

FOREIGN PATENT DOCUMENTS

| | | | |
|---|---|---|---|
| 2729768 | 1/1979 | Fed. Rep. of Germany | 128/203.27 |

*Primary Examiner*—Henry J. Recla

*Attorney, Agent, or Firm*—Robert E. Wagner; Alan L. Barry

[57] ABSTRACT

A linear, annular flow nebulizer for use in inhalation therapy comprising a shell having walls with an ambient air intake in one of the walls; a nebulizer conduit having a proximal end, a distal end and a longitudinal fluid passageway, the proximal end communicating with a gas source and the distal end inwardly tapering to define a nozzle which penetrates a wall of the shell; and, a nebulizer cup having a bottom end mounted within the interior space of the shell, the bottom of the cup having a well surrounding a dispensing port spaced from and in alignment with the nozzle, the well permitting the angular confluence of a liquid stream into a gas stream to produce an aerosol. The nebulizer further includes a hollow tapered throat associated with the ambient air intake to draw and mix ambient air with the aerosol; a tubular thermally-conductive core in communication with the throat; a container having an opening for supplying liquid to the nebulizer cup; a closure mounted over the container opening with the core being mounted through the closure; and, a tube connected to the cup and extending into the container to conduct liquid into the cup.

5 Claims, 2 Drawing Figures

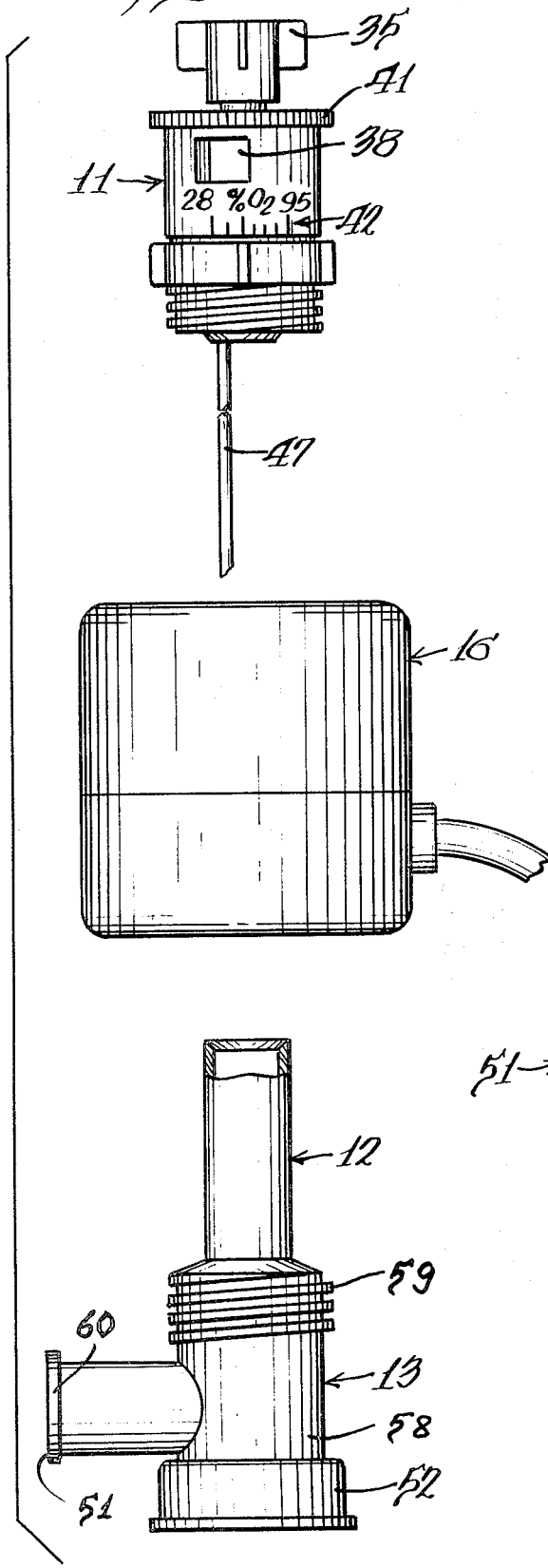
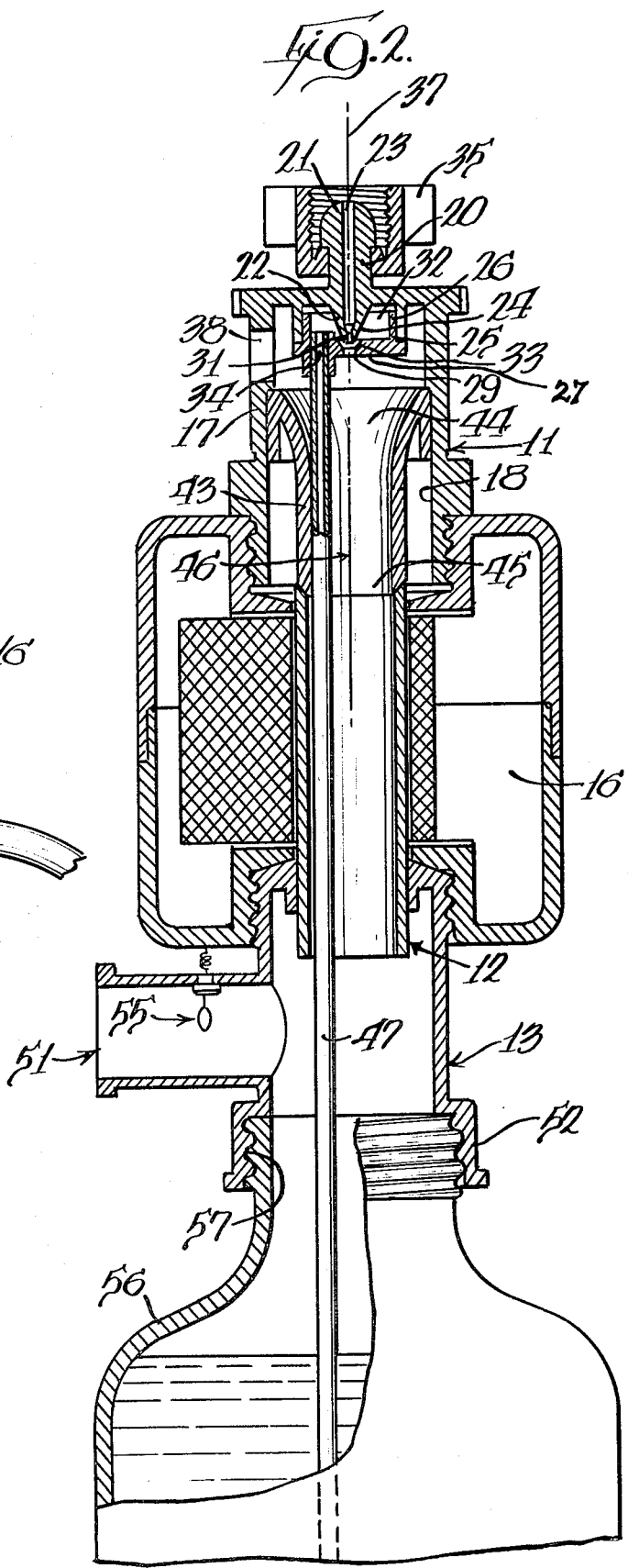

ANNULAR FLOW ENTRAINMENT NEBULIZER

TECHNICAL FIELD

This invention relates to inhalation therapy and more particularly to an aerosol producing means in the form of an improved nebulizer for attachment to a replaceable liquid source container.

BACKGROUND OF THE INVENTION

Inhalation therapy is the medical art of treating a patient with oxygen, or a mixture of air and oxygen, having a high moisture content. This is generally accomplished by atomizing or nebulizing pure water or an aqueous physiological saline solution by use of pressurized oxygen. As the oxygen flows through an orifice or venturi it creates a negative pressure which draws a liquid such as water into a nebulizer. The oxygen stream breaks the water flow into fine particles to form an aerosol which passes along an outlet hose to the patient. In some cases the aerosol is mixed with ambient air and warmed before being sent to the patient.

A variety of mechanical nebulizers are known and are illustrated by U.S. Pat. Nos. 3,915,386 to Vora, 4,150,071 to Pecina, 3,771,721 to Van Amerongen, 3,864,544 to Van Amerongen, 3,652,015 to Beall, 4,178,334 to Miller, 4,195,044 to Miller and 4,231,973 to Young et al. Nebulizers currently in use also provide a heated aerosol to the patient's lungs. Most nebulizers usually require the use of special containers to serve as a liquid source. Other nebulizers are either too expensive to be disposable or are difficult to resterilize and clean after use. Existing nebulizers are also limited in the moisture output and minimum oxygen concentrations which they can provide.

Accordingly it is desirable to provide a nebulizer which has disposable and easily sterilizable parts, and is efficient in producing a high moisture output and desirable, relatively low oxygen concentrations.

SUMMARY OF THE INVENTION

The present invention provides a nebulizer having a design which efficiently produces an oxygen and air mixture having a relatively high moisture content.

The nebulizer assembly has a nebulizer head for combining oxygen, ambient air and water to form an inhalation mixture. The nebulizer head is removably mounted on a core which can be heated to warm the mixture. Mounted on the core is a discharge assembly to deliver the inhalation mixture to the patient.

The nebulizer head of the present invention operates by passing a pressurized gas such as oxygen through a conduit terminating in a nozzle provided with an orifice. Extending around the nozzle and defining a chamber is a nebulizer cup having a dispensing port adjacent to and substantially aligned with the nozzle. The nozzle orifice is spaced from the dispensing port. Preferably the nozzle orifice is smaller in diameter than the dispensing port and, more preferably, is spaced approximately one dispensing port diameter from the dispensing port. The cup is also provided with a liquid inlet in communication with a liquid source to provide liquid to the chamber. As the pressurized oxygen passes through the nozzle orifice it creates a localized region of negative pressure around the nozzle orifice creating a negative pressure in the chamber which draws a liquid, such as sterilized water, through the inlet and into the chamber. The liquid then flows around the nozzle and surrounds the oxygen stream from all sides. The oxygen stream breaks the liquid flow into fine particles to produce an aerosol as the oxygen and the liquid pass through the dispensing port and through the assembly.

Unlike previous nebulizers which utilize a venturi tube or two orifices at right angles, the present invention utilizes the forces generated all around the flowing gas stream for drawing the water rather than the force from just one sector of the stream. Also unlike previous systems, the aerosol stream that is produced is not deflected and dispersed by impingement upon a right angle orifice or upon a right angle baffle or baffles. The result is a well-defined stream of aerosol which has more flow (kinetic) energy than other systems, as well as maximizing entrainment to produce a higher nebulized liquid, i.e., mist, content. The produced, better-defined aerosol stream is more effective in drawing in ambient air and therefore produces an inhalation mixture having relatively lower oxygen concentrations, as compared to previous nebulizers.

As the aerosol passes through a throat or venturi means it draws ambient air in through an air intake in the head and then combines with the ambient air to produce the inhalation mixture. The nebulizer may also be provided with a heated core to regulate the temperature of the produced inhalation mixture before this mixture is sent to the patient via the discharge assembly. The higher mist content produced by this device permits the inhalation mixture to be heated to a higher temperature, closer to body temperature. Previous nebulizers generally only reach 80–85 degrees F. Any liquid not completely nebulized returns to the liquid container under the force of gravity.

In the preferred embodiment, the nebulizer is constructed in more than one section. A disposable nebulizer head which includes the nozzle and throat is removably mounted on a sterilizable core and discharge assembly. This reduces the cost of the system and allows reuse of easy to clean portions, thus reducing the total cost of treatment to the patient as well.

Numerous other advantages and features of the present invention will become readily apparent from the following detailed description of the invention, drawings, and the appended claims.

BRIEF DESCRIPTION OF THE DRAWINGS

FIG. 1 is an exploded elevational view showing the nebulizer of the present invention comprising a nebulizer head, heater assembly, and discharge assembly; and FIG. 2 is an enlarged cross-sectional elevational view showing the interior of the nebulizer embodying the present invention.

DESCRIPTION OF THE PREFERRED EMBODIMENT

This invention may be used in many different forms. The specification and accompanying drawings disclose only one specific form as an example of the use of the invention. The invention is not intended to be limited to the embodiment illustrated, and the scope of the invention will be pointed out in the appended claims. The precise shapes and sizes of the components described are not essential to the invention unless otherwise indicated. For ease of description the apparatus of this invention will be described in a normal upright position and such terms as above, below, etc. will be used in reference to this position. It will be understood, however, that the apparatus of this invention may be manufactured, stored, transported and adapted to be used in an orientation other than the position described.

Referring to FIG. 1, the nebulizer of the present invention in its preferred embodiment comprises a nebulizer head 11, core 12 and discharge assembly 13. Positioned around the core 12 is an electronically controlled heat source 16 which heats the surface of the core which in turn transfers heat to an inhalation mixture passing through the core.

Referring now to FIG. 2, the nebulizer head 11 is comprised of an elongated shell member or shell 17 defining an interior space 18, a nebulizer conduit 20, a nebulizer cup 25 and a venturi means such as throat 43. The nebulizer conduit 20 having a proximal end 21 and a distal end 22 defining a nozzle 24, is mounted on the shell 17 with the nozzle extending into the space defined by the shell. A fluid passageway 23 extends longitudinally between the ends and is in fluid communication with a nozzle orifice 31 at the distal end 22. Walls 26 of the nebulizer cup 25 are positioned axially around the nozzle 24. The nebulizer cup 25 also has a bottom 27 which defines a dispensing port 29 spaced from and in substantial axial alignment with the nozzle orifice 31. The cup 25 may also define a well 33 that surrounds the dispensing port 29.

The nebulizer cup 25 defines a chamber 32 around the nozzle 24. The cup 25 and chamber 32 can have any shape provided the chamber substantially surrounds the nozzle. Preferably the cup 25 defines an annular chamber. The cup also includes an inlet 34 to place the chamber in fluid communication with a liquid source to provide liquid to the chamber.

In the preferred embodiment the nozzle orifice 31 has a diameter of about 0.015 inches to about 0.025 inches (about 0.38 to about 0.64 millimeters) and the dispensing port 29 has a diameter of about 0.020 to about 0.040 inches (about 0.51 to about 0.89 millimeters). The orifice 31 preferably is larger than the port 29 and is spaced about 0.020 inches to about 0.040 inches (about 0.51 to about 1.02 millimeters), or more preferably about one port diameter, from the port. However, the nozzle 24 and orifice 31 may extend into the well 33. In any event, nozzle orifice 31 and dispensing port 29 are substantially in alignment with one another but spaced so as to provide an annular flow of the liquid to be nebulized around the gas stream emanating when the liquid is contained in the cup 25.

The proximal end 21 of the nebulizer conduit 20 defines an attachment means 35 to place a pressurized gas source (not shown) in fluid communication with the passageway 23 and the orifice 31. An imaginary line that passes through the center of the orifice 31 and the center of the port 29 defines a flow axis 37 for a gas or aerosol stream produced when the pressurized gas source is activated.

The head 11 is provided with an air intake 38 to allow outside ambient air to enter the interior space 18. The size of the air intake 38 and hence the amount of ambient air allowed into the interior space 18 is controlled by a regulating means 41 which has a display 42 indicating the air to aerosol mixture. Oxygen concentrations as low as about 28 volume percent oxygen can be achieved in this manner.

The hollow tapered throat 43 having a large end 44, a small end 45 and a longitudinal axis 46 can be mounted in the nebulizer head 11 below or distal the cup port 29 with the large end toward the port. Throat 43 can be a venturi-type device that causes ambient air to be drawn into the nebulizer head for mixing with the produced aerosol. In the preferred embodiment the flow axis 37 passes through the hollow portion of the throat 43 thus allowing a straight flow passageway to efficiently mix the ambient air with the aerosol.

In operation, a pressurized gas source such as an oxygen tank (not shown) is connected to the attachment means 35. The oxygen then passes through the fluid passageway 23 to the orifice 31. As the oxygen passes through the orifice 31 a local negative pressure is generated in the vicinity of the orifice by the Bernoulli effect. This negative pressure generates a negative pressure in the annular chamber 32 which draws liquid from a liquid source, (usually a screw-top container such as container 56), up a dip tube 47 through the inlet 34 and into the annular chamber. The liquid then flows around the nozzle 24 and surrounds the oxygen stream from all sides. The oxygen stream from nozzle 24 draws the liquid around the nozzle 24 and through the port 29, breaking up the liquid into fine particles to produce an aerosol stream. As the stream of aerosol enters the tapered throat 43, another negative pressure region is created which draws ambient air through the air intake 38. The aerosol mixes with the ambient air as they pass through the throat producing an inhalation mixture. The regulating means 41 is set to allow in the proper amount of ambient air to achieve the desired oxygen content in the final inhalation mixture.

The design of the present invention is particularly effective because the aerosol and the aerosol-air mixtures are all created by one linear stream having more energy than in other nebulizer systems. Since more ambient air can be drawn in with the system embodying the present invention, it becomes possible to reach lower oxygen concentrations than previous systems.

The nebulizer head 11, where the aerosol is initially produced, can be made as a disposable unit and removably mounted on the core 12. Thus unlike other units which call for the disposal of the entire unit, in a nebulizer of the present invention only those parts which are difficult to clean or not easily sterilized need to be disposed of. The core 12 and discharge assembly 13 can be readily cleaned and reused. This particular combination of disposable and reusable parts optimizes cost effectiveness, aseptic design, and convenience, thus increasing the cost effectiveness of inhalation therapy.

As the ambient air-aerosol mixture passes out of the heat 11 through the throat 43 and into the core 12 the mixture can be heated to a desired temperature by an electronically controlled heat source 16 positioned about the core as is well known in the art. Some of the small liquid droplets that impinge on the core can also be vaporized, wholly or in part, thereby providing further heat input to the inhalation mixture, if desired. This together with the high mist content of the inhalation mixture allows the mixture to reach higher temperatures approaching body temperature of 98.6 degrees F. (37 degrees C.) without overheating the liquid in dip tube 47 and attendant undesirable steam generation therein. The core 12 is constructed of material having good heat transfer characteristics such as stainless steel. The core 12 is shown together with the discharge assembly 13 in FIG. 1. As the mixture leaves the core 12, it enters the removably mounted discharge assembly 13 and exits the nebulizer through a side outlet means, such as outlet 51, to be delivered to the patient. The outlet may be provided with a temperature sensor 55 associated with the heat source 16 to control the temperature of the inhalation mixture.

The discharge assembly 13 which can be made of a heat sterilizable material comprises a hollow tee member 58 constituted by a first, second and third hollow leg. The distal end of the first leg terminates in an externally threaded connector means 59 adapted to engage the heat source 16 and slidably receive the core 12. The distal end of the second leg terminates in an internally threaded container attachment means 52 to allow the nebulizer to be mounted on a liquid source container such as a standard bottle 56 with a threaded top portion 57 to provide the water or other liquid medication that is to be nebulized. The first and second legs are coaxial and the third leg is substantially normal to the axis of the first and second leg. The distal end of the third leg terminates in an outwardly extending flange 60 and defines the outlet 51.

In operation, not all of the liquid drawn through the port 29 is nebulized. Some of the nebulized liquid may also coalesce into undesirably large particles or droplets. Thus it is beneficial if this unnebulized or coalesced liquid produced can be returned to the liquid source container to be redrawn into the annular chamber 32. As can be seen in FIG. 2 the container attachment means 52 is located in a position of lower potential energy relative to the core, i.e. below, thus allowing any excess liquid or large liquid particles to return to the liquid source container 56. The liquid can then pass from the liquid source container up through the tube 47 to the annular chamber 32.

The foregoing specification is intended as illustrative and not to be taken as limiting. Still other variations within the spirit and scope of this invention are possible and will readily present themselves to those skilled in the art.

I claim:

1. An entrainment nebulizer adapted for use in inhalation therapy, the nebulizer comprising:
   (a) a shell having walls defining an interior space and an ambient air intake through one of the walls;
   (b) a nebulizer conduit having a proximal end and a distal end and a longitudinal fluid passageway between the ends, the proximal end having an attachment means to place the passageway in fluid communication with an external pressurized gas source, the distal end inwardly tapering to define a nozzle having an orifice in fluid communication with the passageway, the conduit being mounted to penetrate a wall of the shell so that at least the nozzle extends into the interior space;
   (c) a nebulizer cup having a bottom and being mounted within the interior space of the shell to axially surround the nozzle to define an annular chamber around the nozzle, the bottom of the cup having a concave depression defining a well, the nozzle protruding to a predetermined depth into the well, the well surrounding a dispensing port selectively spaced from and in substantial alignment with the nozzle orifice, the cup also having an inlet to receive a liquid source, and the well and the port being spatially associated with the nozzle orifice to develop an aerosol flow produced by the confluence of fluid streams from the pressurized gas source and the liquid source, the well permitting the angular confluence of the liquid stream into the gas stream enhancing nebulization of the liquid stream;
   (d) a hollow tapered throat having a large end and a small end being mounted within the shell distal from the port with the large end directed toward the port, the throat operably associated with the air intake to draw ambient air through the intake and mix the ambient air with the aerosol to produce an inhalation mixture;
   (e) a thermally-conductive tubular core having a first end removably seated against the small end of the throat and a second end, the core being in fluid communication with the throat to receive and further conduct the inhalation mixture, the shell, nebulizer conduit, nebulizer cup and throat defining a nebulizer head;
   (f) a container having an opening for supplying the liquid source to the nebulizer head, a closure mounted over said container opening, the second end of said core being mounted through said closure such that said core and throat are in alignment with said container opening whereby said container is in fluid communication with the throat and sealably mounted to the nebulizer head;
   (g) said closure having an outlet in fluid communication with the core to dispense the inhalation mixture; and,
   (h) a tube connected to the cup inlet and extending into the container to conduct the liquid source into the chamber.

2. The entrainment nebulizer of claim 1 wherein the nozzle orifice is spaced from the dispensing port by about one dispensing port diameter.

3. The entrainment nebulizer of claim 1 wherein the closure includes a discharge assembly comprising:
   (a) a hollow member constituted by first, second and third hollow legs joined together to be in fluid communication with each other and to conduct fluid in each leg, the first and the second of said legs being coaxial and the third leg being positioned substantially normal to the axis of the first and second leg;
   (b) a distal end of said first leg terminating in an externally threaded connector means and being provided with an internal sleeve for slidably receiving the tubular core;
   (c) a distal end of said second leg terminating in an internally threaded container attachment means for attachment to the container; and
   (d) a distal end of said third leg extending outwardly to form the outlet.

4. The entrainment nebulizer of claim 1 wherein the nozzle orifice has a diameter less than or equal to the diameter of the dispensing port.

5. The entrainment nebulizer of claim 1 wherein the well has an inverted frusto-conical shape.

* * * * *